(12) United States Patent
Cella et al.

(10) Patent No.: US 6,291,700 B1
(45) Date of Patent: Sep. 18, 2001

(54) METHOD FOR PREPARING STERICALLY HINDERED PHOSPHORAMIDATES

(75) Inventors: James Anthony Cella; John Robert Campbell, both of Clifton Park; Paul Edward Howson, Latham, all of NY (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 09/538,882

(22) Filed: Mar. 30, 2000

Related U.S. Application Data

(60) Provisional application No. 60/135,755, filed on May 25, 1999.

(51) Int. Cl.$^7$ .................................................. C07F 9/08
(52) U.S. Cl. ............................ 558/138; 558/37; 544/337
(58) Field of Search ............................ 544/337; 558/73, 558/138

(56) References Cited

U.S. PATENT DOCUMENTS

| | | |
|---|---|---|
| 3,868,376 | 2/1975 | Hotten . |
| 4,668,720 | 5/1987 | Kauth et al. . |
| 5,973,041 | 10/1999 | Campbell et al. . |

FOREIGN PATENT DOCUMENTS

| | | |
|---|---|---|
| 1349469 | 4/1974 | (GB) . |
| 7-70158 | 3/1995 | (JP) . |
| 10175985 | 6/1998 | (JP) . |
| WO 93/22373 | 11/1993 | (WO) . |

OTHER PUBLICATIONS

CA:76:72147 abs of Chim Ther. by Savignac et al 6(5) pp 380–3, 1971.*
CA:76:13978 abs of J Chem Soc C by Edmundson (21) pp 3614–17, 1971.*
CA:109:93150 abs of Indian J Chem Sect D by Divakar et al 26B (6) pp 546–9, 1987.*
CA:108:167600 abs of J Chem Eng Data by Talley 33(2) pp 221–2, 1988.*
John J. Talley, "Preparation of Sterically Hindered Phosphoramidates", J. Chem. Engr. Data, vol. 33, pp.221–222, 1988.
U.S. Application No. 09/511,561, filed Feb. 23, 2000.
U.S. Application No. 09/515,801, filed Feb. 29, 2000.

* cited by examiner

*Primary Examiner*—Gary Geist
(74) *Attorney, Agent, or Firm*—S. Bruce Brown; Noreen C. Johnson

(57) ABSTRACT

Sterically hindered phosphoramidates such as N,N'-bis[di-(2,6-xylyl)phosphoryl]piperazine are prepared by the reaction of a sterically hindered diaryl chlorophosphate, such as di-(2,6-xylyl) chlorophosphate, with a basic nitrogen compound containing at least two basic N—H groups, preferably a heterocyclic compound such as piperazine, in the presence of an acid acceptor such as triethylamine. The reaction is conducted in methylene chloride or an aromatic hydrocarbon such as toluene as solvent. If an aromatic hydrocarbon is employed, there is also present at least one dipolar aprotic nitrogen compound, such as 4-dimethylaminopyridine, in an amount effective to increase the reaction rate.

17 Claims, No Drawings

METHOD FOR PREPARING STERICALLY HINDERED PHOSPHORAMIDATES

CROSS-REFERENCE TO RELATED APPLICATIONS

This application claims priority from provisional application Ser. No. 60/135,755 filed May 25, 1999.

BACKGROUND OF THE INVENTION

This invention relates to the preparation of phosphoramidates, and more particularly to their preparation from nitrogen bases and diaryl chlorophosphates.

The use of sterically hindered phosphoramidates such as N,N'-bis[di-(2,6-xylyl)phosphoryl]piperazine (hereinafter sometimes "XPP") as flame retardant additives for synthetic resins, especially thermoplastic resins such as polycarbonates, ABS resins and blends thereof, has been discovered to have particular advantages including improved high temperature stability of the resulting blends. Reference is made, for example, to U.S. Pat. No. 5,973,041 and to copending, commonly owned applications Ser. Nos. 09/235,679 and 09/364,915.

XPP and analogous compounds may be conveniently prepared by the reaction of a diaryl chlorophosphate, such as di-(2,6-xylyl) chlorophosphate, with a heterocyclic compound containing at least two basic N-H groups, such as piperazine. According to the prior art as illustrated by Talley, *J. Chem. Eng. Data*, 33, 221–222 (1983), this reaction may be conducted in chloroform as solvent, in the presence of triethylamine as an acid acceptor. The triethylamine is employed in stoichiometric amount or in excess, and reacts with the by-product hydrogen chloride to drive the reaction to completion.

The Talley paper describes the preparation of a number of analogous compounds including those derived from such nitrogen compounds as benzylamine, cyclohexylamine, aniline, ethylenediamine and p-phenylenediamine as well as piperazine. Reported yields were as high as 90% for the reaction with aniline, and as low as 61% for the reaction with p-phenylenediamine. Piperazine afforded XPP in a yield of only 68%, one of the lowest reported.

If the use of XPP as a flame retardant additive is to be commercially feasible, it is necessary to improve its yield by a significant amount. Also, it is desirable to minimize use of the relatively toxic solvent chloroform on a commercial scale.

It is of interest, therefore, to develop high-yield methods employing relatively harmless materials for the preparation of XPP and analogous compounds.

SUMMARY OF THE INVENTION

The present invention is based on the discovery that solvents other than chloroform, in particular methylene chloride and aromatic hydrocarbons, may be employed for the preparation of sterically hindered phosphoramidates in high yield from sterically hindered diaryl chlorophosphates and nitrogen bases. In the case of aromatic hydrocarbons, yields are significantly improved if a catalyst is present.

Accordingly, in one embodiment the invention is a method for preparing a sterically hindered phosphoramidate which comprises contacting a sterically hindered diaryl chlorophosphate with a basic nitrogen compound containing at least two basic N—H groups in the presence of at least one acid acceptor and at least one solvent selected from the group consisting of methylene chloride and aromatic hydrocarbons, with the proviso that if the solvent is at least one aromatic hydrocarbon there is also present a reaction rate increasing proportion of at least one dipolar aprotic nitrogen compound.

In another embodiment the invention is a method for preparing a sterically hindered phosphoramidate which comprises contacting a sterically hindered diaryl chlorophosphate with a basic nitrogen compound containing at least two basic N—H groups in the presence of at least one acid acceptor and at least one solvent selected from the group consisting of methylene chloride and aromatic hydrocarbons, with the proviso that if the solvent is at least one aromatic hydrocarbon there is also present a reaction rate increasing proportion of at least one dipolar aprotic nitrogen compound, said phosphoramidate having a glass transition temperature of at least about 0° C., preferably of at least about 10° C., and most preferably of at least about 20° C.

DETAILED DESCRIPTION; PREFERRED EMBODIMENTS

Within the context of the present invention a sterically hindered phosphoramidate is one in which at least one aryl substituent linked to heteroatom-phosphorus has at least one substituent on the aryl ring ortho to the aryl-heteroatom-phosphorus linkage. The sterically hindered diaryl chlorophosphates include those having the formula I

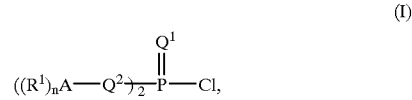

wherein A is an aromatic group, each $R^1$ is independently alkyl, aryl or halo, $Q^1$ is oxygen or sulfur, $Q^2$ is oxygen, sulfur, or $NR^1$, and n has the value of 1 up to the number of free valency sites on the aromatic ring and at least one $R^1$ substituent on the aryl ring is ortho to the heteroatom-phosphorus linkage. Preferably, A is a phenyl ring and n has the value of 1–5. Preferably, each $R^1$ is $C_{1-4}$ primary or secondary alkyl; most preferably, methyl, and n is 2 with each substituent ortho to the phosphorus linkage.

Preferred sterically hindered diaryl chlorophosphates include those having the formula II:

wherein A is an aromatic radical, each $R^1$ is independently alkyl, aryl or halo, n is from 1 to the number of free valency sites on the aromatic ring(s) and at least one $R^1$ moiety is ortho to the O-P linkage. Preferably, A is a phenyl ring and n is 1–5. More preferably, each $R^1$ is $C_{1-4}$ primary or secondary alkyl, most preferably methyl, and n is 2 or 3 with two substituents ortho to the O-P linkage. Particularly preferred chlorophosphates are di-(2,4,6-trimethylphenyl) chlorophosphate and di-(2,6-dimethylphenyl) chlorophosphate, also known as di-(2,6-xylyl) chlorophosphate.

Any compound, acyclic or cyclic, containing at least two basic N—H groups may be employed. Suitable compounds include those of the formula III

$$R^2NH-CH_2CH_2-NHR^2, \quad (III)$$

wherein each $R^2$ is a $C_{1-4}$ primary or secondary alkyl radical or both $R^2$ radicals taken together are ethylene. Illustrative acyclic compounds are N,N'-dimethylethylenediamine and N,N'-diethylethylenediamine. Heterocyclic compounds are generally preferred; they are illustrated by piperazine and 1,2,3,4-tetrahydroquinoxaline, both unsubstituted and substituted. Piperazine is most preferred.

In a preferred embodiment, the method of the invention may be used to produce a phosphoramidate having a glass transition temperature of at least about 0° C., preferably of at least about 10° C., and most preferably of at least about 20° C. In particular, the method of the invention may be used to produce a phosphoramidate of the formula IV:

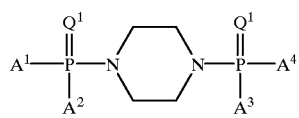
(IV)

wherein each $Q^1$ is independently oxygen or sulfur; and each of $A^{1-4}$ is independently an alkyloxy, alkylthio, aryloxy, or arylthio residue, or an aryloxy or arylthio residue containing at least one alkyl or halogen substitution, or mixture thereof; or an amine residue. In an especially preferred embodiment of the invention, each $Q^1$ is oxygen, and each $A^{1-4}$ moiety is a 2,6-dimethylphenoxy moiety or a 2,4,6-trimethylphenoxy moiety. These phosphoramidates are piperazine-type phosphoramidates. In the above formula wherein each $Q^1$ is oxygen, and each $A^{1-4}$ moiety is a 2,6-dimethylphenoxy moiety, the glass transition temperature of the phosphoramidate is about 62° C. and the melting point is about 192° C.

In another preferred embodiment, the method of the invention may be used to produce a phosphoramidate having a glass transition temperature of at least about 0° C., preferably of at least about 10° C., and most preferably of at least about 20° C., of the formula V:

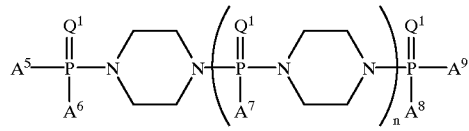
(V)

wherein each $Q^1$ is independently oxygen or sulfur; and each of $A^{5-9}$ is independently an alkyloxy, alkylthio, aryloxy, or arylthio residue, or an aryloxy or arylthio residue containing at least one alkyl or halogen substitution, or mixture thereof; or an amine residue; and n is from 0 to about 5. In a more preferred embodiment, each $Q^1$ is oxygen, and each $A^{5-9}$ moiety is independently phenoxy, 2,6-dimethylphenoxy, or 2,4,6-trimethylphenoxy, and n is from 0 to about 5.

In another embodiment the method of the invention may be used to produce a phosphoramidate having a glass transition temperature of at least about 0° C., preferably of at least about 10° C., and most preferably of at least about 20° C., of the formula VI:

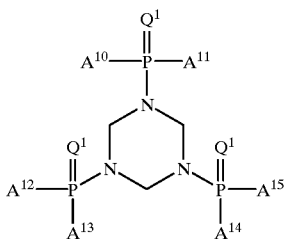
(VI)

wherein each $Q^1$ is independently oxygen or sulfur; and each of $A^{10-15}$ is independently an alkyloxy, alkylthio, aryloxy, or arylthio residue, or an aryloxy or arylthio residue containing at least one alkyl or halogen substitution, or mixture thereof; or an amine residue. In a more preferred embodiment, each $Q^1$ is oxygen, and each $A^{10-15}$ moiety is independently phenoxy, 2,6-dimethylphenoxy, or 2,4,6-trimethylphenoxy.

In another embodiment the method of the invention may be used to produce a phosphoramidate having a glass transition temperature of at least about 0° C., preferably of at least about 10° C., and most preferably of at least about 20° C., of the formula VI:

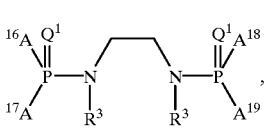
(VII)

wherein each $Q^1$ is independently oxygen or sulfur; each of $A^{6-19}$ is independently an alkyloxy, alkylthio, aryloxy, or arylthio residue, or an aryloxy or arylthio residue containing at least one alkyl or halogen substitution, or mixture thereof; or an amine residue; and each $R^3$ is an alkyl radical, or both $R^3$ radicals taken together are an alkylidene or alkyl-substituted alkylidene radical. In a preferred embodiment, each $Q^1$ is oxygen; both $R^3$ radicals taken together are an unsubstituted $(CH_2)_m$ alkylidene radical, wherein m is 2 to 10; and each $A^{16-19}$ moiety is independently phenoxy, 2,6-dimethylphenoxy, or 2,4,6-trimethylphenoxy. In a more preferred embodiment, each $Q^1$ is oxygen; each $R^3$ is methyl; and each $A^{16-19}$ moiety is independently phenoxy, 2,6-dimethylphenoxy, or 2,4,6-trimethylphenoxy.

In another embodiment the method of the invention may be used to produce a phosphoramidate having a glass transition point of at least about 0° C., preferably of at least about 10° C., and most preferably of at least about 20° C., of the formula VIII:

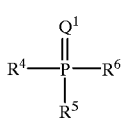
(VIII)

wherein $Q^1$ is oxygen or sulfur, and $R^4$ is of the formula IX:

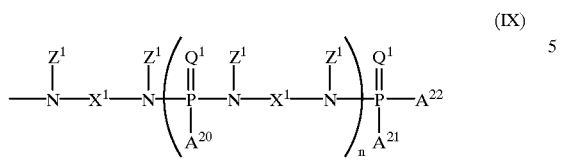

wherein each $Q^1$ is independently oxygen or sulfur; each of $A^{20-22}$ is independently an alkyloxy, alkylthio, aryloxy, or arylthio residue, or an aryloxy or arylthio residue containing at least one alkyl or halogen substitution, or mixture thereof; or an amine residue; each $Z^1$ is an alkyl radical, aromatic radical, or aromatic radical containing at least one alkyl or halogen substitution or mixture thereof; each $X^1$ is an alkylidene radical, aromatic radical, or aromatic radical containing at least one alkyl or halogen substitution or mixture thereof; n is from 0 to about 5; and $R^5$ and $R^6$ are each independently an alkyloxy, alkylthio, aryloxy, or arylthio residue, or an aryloxy or arylthio residue containing at least one alkyl or halogen substitution, or mixture thereof; or an amine residue. In a preferred embodiment, each $Q^1$ is oxygen; each $A^{20-22}$ moiety is independently phenoxy, 2,6-dimethylphenoxy, or 2,4,6-trimethylphenoxy; each $Z^1$ is methyl or benzyl; each $X^1$ is an alkylidene radical containing 2–24 carbon atoms; n is from 0 to about 5; and $R^5$ and $R^6$ are each independently phenoxy, 2,6-dimethylphenoxy, or 2,4,6-trimethylphenoxy.

In another embodiment the method of the invention may be used to produce a phosphoramidate having a glass transition point of at least about 0° C., preferably of at least about 10° C., and most preferably of at least about 20° C., of the formula X:

wherein $Q^1$ is oxygen or sulfur; and $R^7$ is of the formula XI:

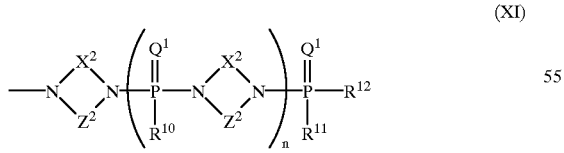

wherein each $Q^1$ is independently oxygen or sulfur; each $X^2$ is an alkylidene or alkyl-substituted alkylidene residue, aryl residue, or alkaryl residue; each $Z^2$ is an alkylidene or alkyl-substituted alkylidene residue; each of $R^{10}$, $R^{11}$, and $R^{12}$ is independently an alkyloxy, alkylthio, aryloxy, or arylthio residue, or an aryloxy or arylthio residue containing at least one alkyl or halogen substitution, or mixture thereof; or an amine residue; n is from 0 to about 5; and $R^8$ and $R^9$ are each independently an alkyloxy, alkylthio, aryloxy, or arylthio residue, or an aryloxy or arylthio residue containing at least one alkyl or halogen substitution, or mixture thereof; or an amine residue.

In a preferred embodiment, each $Q^1$ is oxygen; each $X^2$ is an alkylidene or alkyl-substituted alkylidene residue; each $Z^2$ is an alkylidene or alkyl-substituted alkylidene residue; each of $R^8$, $R^9$, $R^{10}$, $R^{11}$, and $R^{12}$ is independently phenoxy, 2,6-dimethylphenoxy, or 2,4,6-trimethylphenoxy; and n is from 0 to about 5. In a more preferred embodiment, each $Q^1$ is oxygen; each $X^2$ and $Z^2$ is independently an unsubstituted alkylidene residue of the form $(CH_2)_m$, wherein m is 2 to 10; each of $R^8$, $R^9$, $R^{10}$, $R^{11}$, and $R^{12}$ is independently phenoxy, 2,6-dimethylphenoxy, or 2,4,6-trimethylphenoxy; and n is from 0 to about 5. In an especially preferred embodiment, the phosphoramidate is derived from piperazine (i.e. $X^2$ and $Z^2$ are each $—CH_2—CH_2—$).

In another preferred embodiment, the method of the invention may be used to produce a cyclic phosphoramidate having a glass transition point of at least about 0° C., preferably of at least about 10° C., and most preferably of at least about 20° C. of the formula XII:

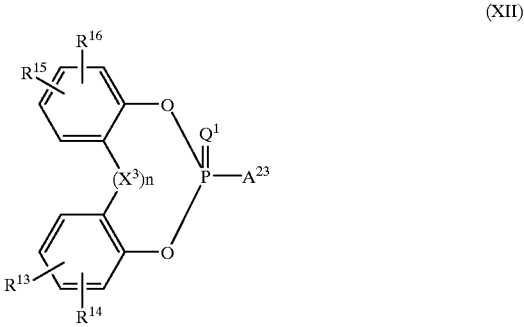

wherein each of $R^{13-16}$ is independently a hydrogen or an alkyl radical, $X^3$ is an alkylidene radical, $Q^1$ is oxygen or sulfur, and $A^{23}$ is a group derived from a primary or secondary amine having the same or different radicals that can be aliphatic, alicyclic, aromatic, or alkaryl, or $A^{23}$ is a group derived from a heterocyclic amine, or $A^{23}$ is a hydrazine compound. Preferably $Q^1$ is oxygen. It should be noted that when n is 0, then the two aryl rings are linked together at that site (i.e. where $X^3$ is absent) by a single bond in the positions ortho,ortho' to the phosphoryl bonds.

In another preferred embodiment, the method of the invention may be used to produce a bis(cyclic) phosphoramidate having a glass transition point of at least about 0° C., preferably of at least about 10° C., and most preferably of at least about 20° C. of the formula XIII:

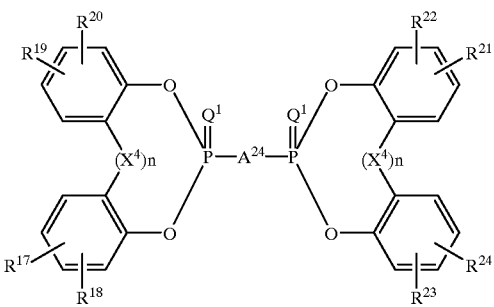

(XIII)

wherein $Q^1$ is oxygen or sulfur; each of $R^{12-24}$ is independently a hydrogen or an alkyl radical; $X^4$ is an alkylidene radical; m and n are each independently 0 or 1; and $A^{24}$ is

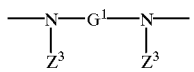

wherein $G^1$ is sulfur, an alkylidene radical, alkyl-substituted alkylidene radical, aryl radical, or alkaryl radical, and each $Z^3$ is independently an alkyl radical, an aryl radical, or an aryl radical containing at least one alkyl or halogen substitution, or mixture thereof; or wherein $A^{24}$ is

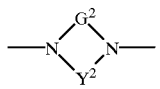

wherein $G^2$ is alkylidene, aryl, or alkaryl, and $Y^2$ is alkylidene or alkyl-substituted alkylidene. Preferred phosphoramidates are those wherein $Q^1$ is oxygen, $A^{24}$ is a residue of piperazine, and the phosphoramidate has a plane of symmetry through $A^{24}$. Highly preferred phosphoramidates include those wherein $Q^1$ is oxygen; $A^{24}$ is a residue of piperazine; the phosphoramidate has a plane of symmetry through $A^{24}$; at least one R substituent on each aryl ring is a methyl adjacent to the oxygen substituent; n and m are each 1; and $X^4$ is $CHR^{25}$ wherein $R^{25}$ is a hydrogen or an alkyl residue of from about 1 to about 6 carbon atoms. It should be noted that when either or both of m or n is 0, then the two aryl rings are linked together at that site (i.e. where $X^4$ is absent) by a single bond in the positions ortho,ortho' to the phosphoryl bonds.

The method may also be used to make phosphoramidates with intermediate glass transition temperatures by using a mixture of various substituted and non-substituted aryl moieties within the phosphoramidate.

In the present invention, the solvents which may be employed for preparation of the phosphoramidate are methylene chloride and aromatic hydrocarbons, the latter being exemplified by toluene and the isomeric xylenes. Mixtures of these solvents may also be employed. It has unexpectedly been found that despite their similarity in molecular structure, chloroform and methylene chloride differ substantially in the yield of phosphoramidate produced. While the yield in chloroform was only 68%, levels above 90% can be obtained with the use of methylene chloride. It is preferred that water be excluded from the reaction mixture.

Similarly, substantial yield improvement can be realized with the use of at least one aromatic hydrocarbon as solvent. In this instance, however, it has been noted that the reaction rate is decreased to a pronounced extent. Therefore, in one embodiment of the invention, when aromatic hydrocarbons are used as solvents, at least one dipolar aprotic nitrogen compound may be included as a catalyst in an amount effective to increase the reaction rate. Suitable aprotic nitrogen compounds include 4-dimethylaminopyridine, 4-pyrrolidinopyridine, 4-piperidinopyridine, N-methylpyrrolidinone, dimethylformamide and dimethylacetamide; 4-dimethylaminopyridine (hereinafter sometimes "DMAP") is preferred.

Also present according to the invention is at least one acid acceptor. The preferred acid acceptors are tertiary amines, more preferably trialkylamines, especially those in which the alkyl groups are $C_{2-6}$ primary or secondary alkyl. Triethylamine is preferred.

The method of the invention is typically conducted at temperatures in the range of about 35–150° C., preferably about 40–60° C. An inert atmosphere, such as nitrogen or argon, is preferably employed. Various methods of blending the reagents may be employed. Preferably, the acid acceptor, solvent and basic nitrogen compound are introduced in sequence, or all three are introduced together. When a catalyst is employed, it may be introduced in some sequence with the other reagents or may be added subsequently.

Molar ratios of diaryl chlorophosphate to basic nitrogen compound are generally in the range of about 2.0–2.5:1, preferably about 2.05–2.2:1. Acid acceptor is typically present in excess, most often in a molar ratio to diaryl chlorophosphate of about 1.1–1.5:1 and preferably about 1.1–1.2:1. The dipolar aprotic nitrogen compound, when present, is employed in catalytic amount, most often in the range of about 5–25 mole percent based on basic nitrogen compound.

The progress of the reaction may be monitored by art-recognized analytical methods, such as gas chromatography, high performance liquid chromatography (HPLC), and/or nuclear magnetic resonance spectroscopy. In general, a reaction time on the order of 5–25 hours, preferably 10–20 hours is adequate for the reaction to progress to effective completion. Shorter reaction times are best for maximum productivity. The phosphoramidate may then be isolated by conventional operations, typically including one or more steps of contact with aqueous mineral acid, separation of the organic layer, washing and volatilization of solvent, if necessary.

The invention is illustrated by the following examples.

EXAMPLE 1

A slurry of 11.6 kilograms (kg) (134.82 moles) of piperazine, 33.8 kg (334 moles) of triethylamine and 26 liters of methylene chloride was agitated in a nitrogen atmosphere and pumped at 20° C. over about 1.5 hours, with stirring, to a reactor containing a solution of 184.4 kg (567.3 moles) of di-(2,6-xylyl) chlorophosphate, while maintaining the temperature at 45.6° C. (gentle reflux). The reaction was continued at this temperature for 10 hours.

Visual inspection of the reaction mixture following completion of the reaction revealed the presence of a precipitate, probably the desired product and/or triethylamine hydrochloride. Additional methylene chloride, 140 kg, was added to dissolve the precipitate. Aqueous 1 molar hydrogen chloride solution, 75.7 liters, was added and the mixture was stirred slowly for 10 minutes at 38° C. The phases were allowed to separate for 1.5 hours and the organic phase was removed and saved. Three liters of emulsion and the aqueous phase were discarded. The acid wash step was repeated except that the phases were allowed to settle for only 45 minutes; no emulsion was observed and the aqueous phase was acidic. Deionized water, 75.7 liters, was added and the mixture was stirred for 10 minutes at 38–39° C. The phases were allowed to settle for 40 minutes. Good phase separation was observed. The aqueous phase was discarded and two additional water washes were performed.

The product solution (approximately 245 liters) was returned to the reactor and heated to reflux. About 45 liters of methylene chloride was removed by distillation to concentrate, resulting in a clear solution. While maintaining a solution temperature of approximately 47° C., 235 kg of methanol was slowly added. The solution was allowed to cool overnight and the next day to a final temperature of 6° C., resulting in product crystallization.

The product was gravity fed to a 102 centimeter centrifugal basket filter where it was isolated. The filter cake was spray washed with about 15 liters of methanol. After spin drying in the centrifuge under nitrogen, the product (XPP) was dried in vacuum ovens at 75° C. Final yield was 81.6 kg (92% of theoretical). Purity was shown by reverse phase HPLC to be greater than 99.9%. The product contained less than 1 ppm each of chloride, magnesium, iron and sodium.

EXAMPLE 2

The procedure of Example 1 was repeated, except that the methylene chloride and triethylamine were initially added to the di-(2,6-xylyl) chlorophosphate, after which the piperazine was added portionwise as a solid, at a rate to control the exotherm at 45.6° C. The results were similar.

EXAMPLE 3

Triethylamine, 9.15 grams (g) (91 millimoles [mmol]), was added in a nitrogen atmosphere to a stirred solution of 25.0 g (77 mmol) of di-(2,6-xylyl) chlorophosphate in 50 milliliters (ml) of toluene. At 50° C., 3.15 g (37 mmol) of anhydrous piperazine was added all at once, followed by 0.5g (4.1 mmol) of DMAP. The resulting suspension was heated to 100° C. After 16 hours, analysis of the reaction by HPLC showed that conversion was greater than 95%. The mixture was diluted with 50 ml of toluene and maintained at 70° C. while 100 ml of 1 molar aqueous hydrochloric acid solution was added. The aqueous layer was removed and the organic solution was washed twice at 70° C. with 100 ml of water. The toluene phase was cooled and the XPP which crystallized was filtered and dried. The yield of pure product was 89% of theoretical.

A control reaction, conducted for 10 hours at 100° C. in the absence of DMAP, afforded XPP in only a 60% yield. The difference in reaction time is not considered significant, since the reaction is initially rapid and slows down considerably after about 4–5 hours.

EXAMPLE 4

The procedure of Example 3 was repeated, substituting dimethylformamide (0.25 g, 2.8 mmol) for the DMAP. Similar results and a similar high yield were obtained.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

What is claimed is:

1. A method for preparing a sterically hindered phosphoramidate which comprises contacting a sterically hindered diaryl chlorophosphate with a basic nitrogen compound containing at least two basic N—H groups in the presence of at least one acid acceptor and at least one solvent selected from the group consisting of aromatic hydrocarbons, with the proviso that there is also present a reaction rate increasing proportion of at least one dipolar aprotic nitrogen compound, and wherein the diaryl chlorophosphate has the formula

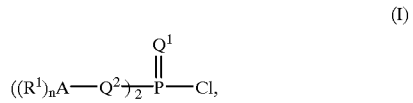

(I)

wherein A is an aromatic radical, each $R^1$ is independently alkyl, aryl or halo, $Q^1$ is oxygen or sulfur, $Q^2$ is oxygen, sulfur, or $NR^1$, n is from 1 to the number of free valency sites on the aromatic ring(s) and at least one $R^1$ substituent on the aryl ring is ortho to the heteroatom-phosphorus linkage.

2. The method according to claim 1 wherein A is phenyl, $Q^1$ and $Q^2$ are oxygen, n is 2 or 3, and each $R^1$ is methyl.

3. The method according to claim 1 wherein the basic nitrogen compound has the formula

wherein each $R^2$ is a $C_{1-4}$ primary or secondary alkyl radical or both $R^2$ radicals taken together are ethylene.

4. The method according to claim 3 wherein the basic nitrogen compound is piperazine.

5. The method according to claim 1 wherein the solvent is toluene.

6. The method according to claim 1 wherein the dipolar aprotic nitrogen compound is 4-dimethylaminopyridine, N-methylpyrrolidinone, dimethylformamide or dimethylacetamide.

7. The method according to claim 6 wherein the dipolar aprotic nitrogen compound is 4-dimethylaminopyridine.

8. The method according to claim 1 wherein the dipolar aprotic nitrogen compound is present in an amount in the range of about 5–25 mole percent based on basic nitrogen compound.

9. The method according to claim 1 wherein the acid acceptor is a tertiary amine.

10. The method according to claim 9 wherein the acid acceptor is triethylamine.

11. The method according to claim 1 wherein contact is carried out at a temperature in the range of about 35–150° C. in an inert atmosphere.

12. The method according to claim 1 wherein the molar ratio of diaryl chlorophosphate to basic nitrogen compound is in the range of about 2.0–2.5:1.

13. The method according to claim 1 wherein the molar ratio of acid acceptor to diaryl chlorophosphate is in the range of about 1.1–1.5:1.

14. A method for preparing a phosphoramidate which comprises contacting a sterically hindered diaryl chlorophosphate with a basic nitrogen compound containing at least two basic N—H groups in the presence of at least one acid acceptor and at least one solvent selected from the group consisting of aromatic hydrocarbons, with the proviso that there is also present a reaction rate increasing proportion of at least one dipolar aprotic nitrogen compound, said phosphoramidate having a glass transition temperature of at least about 0° C.

15. The method of claim 14 in which the phosphoramidate has a glass transition temperature of at least about 10° C.

16. The method of claim 14 which the phosphoramidate has a glass transition temperature of at least about 20° C.

17. A method for preparing N,N'-bis[di-(2,6-xylyl) phosphoryl]piperazine which comprises contacting di-(2,6-xylyl) chlorophosphate with piperazine in the presence of triethylamine as an acid acceptor, toluene as solvent and 4-dimethylaminopyridine in an amount effective to increase the reaction rate.

* * * * *